United States Patent [19]

Frisch

[11] Patent Number: 4,992,312

[45] Date of Patent: Feb. 12, 1991

[54] METHODS OF FORMING PERMEATION-RESISTANT, SILICONE ELASTOMER-CONTAINING COMPOSITE LAMINATES AND DEVICES PRODUCED THEREBY

[75] Inventor: Eldon E. Frisch, Midland, Mich.

[73] Assignee: Dow Corning Wright Corporation, Arlington, Tenn.

[21] Appl. No.: 322,970

[22] Filed: Mar. 13, 1989

[51] Int. Cl.$^5$ .............................................. B29D 22/00
[52] U.S. Cl. .................................. 428/35.7; 427/230; 427/333; 427/336; 427/387; 427/393.5; 427/412.1; 428/412; 428/425.5; 428/447; 623/8
[58] Field of Search .................. 428/35.7, 412, 447, 428/448, 425.5; 427/230, 379, 387, 407.1, 333, 336, 393.5, 412.1; 623/8, 11

[56] References Cited

U.S. PATENT DOCUMENTS

| | | | |
|---|---|---|---|
| 4,163,072 | 7/1979 | Soos | 427/96 |
| 4,172,298 | 10/1979 | Rechenberg | 3/36 |
| 4,247,351 | 1/1981 | Rechenberg | 156/221 |
| 4,249,975 | 2/1981 | Rechenberg | 156/245 |
| 4,258,442 | 3/1981 | Eberl | 3/36 |
| 4,312,920 | 1/1982 | Pierce et al. | 428/425.5 |
| 4,455,691 | 6/1984 | Redinger et al. | 3/36 |
| 4,592,755 | 6/1986 | Penton et al. | 623/8 |
| 4,701,230 | 10/1987 | Loi | 156/145 |

FOREIGN PATENT DOCUMENTS

| | | |
|---|---|---|
| 1199451 | 1/1986 | Canada . |
| 2827076 | 12/1979 | Fed. Rep. of Germany . |
| 2908849 | 9/1980 | Fed. Rep. of Germany . |
| 2827077 | 10/1980 | Fed. Rep. of Germany . |
| 2912120 | 10/1980 | Fed. Rep. of Germany . |
| 144660 | 6/1987 | Japan . |

Primary Examiner—Bernard Pianalto
Attorney, Agent, or Firm—Susan M. Cornwell

[57] ABSTRACT

A method of making a permeation-resistant silicone elastomer-containing laminate useful for making fluid-containing implants such as mammary prostheses and gastric balloons. The method is accomplished by (a) applying a layer of an unvulcanized heat-curable silicone elastomer composition to a cured silicone elastomer substrate, (b) applying a layer of a solvent dispersion of a permeation-resistant elastomer and a solvent on the layer of unvulcanized silicone elastomer composition to form a three-layered laminate, and (c) exposing the three-layered laminate to heat until the unvulcanized silicone elastomer composition is vulcanized. The unvulcanized silicone elastomer composition must be bondable to the cured silicone elastomer substrate, the permeation-resistant elastomer is selected from the group consisting of polyurethane, silicone-polyurethane copolymer, and silicone-polycarbonate copolymer, and the permeation-resistant elastomer solvent must be compatible with both the permeation-resistant elastomer and the unvulcanized silicone elastomer composition.

37 Claims, No Drawings

METHODS OF FORMING PERMEATION-RESISTANT, SILICONE ELASTOMER-CONTAINING COMPOSITE LAMINATES AND DEVICES PRODUCED THEREBY

BACKGROUND OF THE INVENTION

The invention relates to methods of adhering solvent-dilutable polyurethane, silicone-polyurethane copolymer, or silicone-polycarbonate copolymer elastomers to a cured silicone body, and more specifically, to methods of making permeation-resistant laminates from polyurethane, silicone-polyurethane copolymer, or silicone-polycarbonate copolymer elastomers and silicone elastomers and to products produced by such methods.

In the medical field, there is a need for an improved biologically-acceptable, permeation-resistant material which could be used to make items such as the shell or envelope of fluid-filled prostheses or gas- or liquid-filled balloons or balloon portions of other devices. The resistance to permeation of silicone gel, air, or other fluids through the wall of a prosthesis or inflatable device is highly desirable to reduce gradual deflation or unnecessary exposure of tissues surrounding an implanted prosthesis to the permeating interior materials. In the specific case of an air-filled intra-gastric balloon, such as those used to treat morbid obesity, having resistance to the permeation of air through the balloon will decrease deflation and, thus, the need to periodically re-fill the balloon with air.

A breast prosthesis is disclosed in U.S. Pat. No. 4,172,298 which comprises a member formed of an additive cross-linking two-component silicone rubber of an adhesive gelatinous consistency covered on each side by a plastic film, the plastic films being welded to each other along the rim of the member. The patent discloses that polyurethane is particularly useful as the plastic film. U.S. Pat. No. 4,247,351 discloses a process for manufacturing artificial breasts which have cups sheathed by plastic sheets (such as polyurethane) and into which the silicone rubber composition is charged. During the vulcanization of the rubber, the edges of the sheets are forced together and joined by welding. Similarly, U.S. Pat. No. 4,258,442 discloses that a breast prosthesis consisting of silicone rubber may be surrounded by an elastic plastic sheet, especially a foil of polyurethane. Similar to these patents is U.S. Pat. No. 4,701,230 which describes a prosthesis comprising an outer or front sheet, an intermediate sheet, and an inner or rear sheet. The sheets are sealed together at their peripheries. The patent states that the intermediate sheet may be made of polyurethane film. Silicone gel compound is injected into the compartment formed by the outer sheet and the intermediate sheet and is cured.

Similarly, U.S. Pat. No. 4,249,975 discloses a process for manufacturing artificial breasts which uses a two-component silicone rubber composition capable of a crosslinking addition reaction, in which the artificial breast has cups sheathed by plastic sheeting layers (formed of, e.g., polyurethane) initially joined by welding except for one opening through which the silicone composition is introduced under pressure. The silicone composition is then vulcanized and the opening closed by welding.

Some permeation-resistant silicone-gel-filled prostheses are known in the art. Specifically, U.S. Pat. No. 4,455,691 discloses a prosthesis comprising a flexible sac and a silicone gel contained within the sac. The wall of the sac is comprised of a layer of silicone elastomer which substantially impedes the migration of the silicone gel from the sac. Silicone elastomers disclosed as suitable materials for impeding the migration of silicone gel from the sac are composed of reaction products of dimethylpolysiloxane and either 3,3,3,-trifluoropropylpolysiloxane, diphenylpolysiloxane, or methylphenylpolysiloxane. The patent describes that the prosthesis may be made by first making a sac by dipping a mandrel into a solvent dispersion of unvulcanized silicone elastomer, allowing the solvent to evaporate from the coated silicone elastomer, then dipping the coated mandrel into a dispersed elastomer which constitutes a second continuous layer (either layer is formed of the permeation-resistant material). All coats are preferably cured together after the coating has been built up as desired. Alternatively, the prosthesis is said to be made by dipping a mandrel into a dispersion of unvulcanized silicone elastomer, then curing the coated elastomer material to form a sac, then injecting a dispersion of the permeation-resistant material into the cured sac and evenly swirling the dispersion (slush-coating) over the inside of the inflated sac, and then curing the slush-coated sac.

Similarly, Canadian Pat. No. 1,199,451 discloses a silicone-gel-filled silicone rubber container possessing a reduced tendency to exhibit surface-bleed which includes an essentially continuous barrier layer of a composition consisting essentially of a fluorine-containing organopolysiloxane situated between the interior of the container and the gel filling the container.

Although these patents describe permeation-resistant prostheses, there continues to be a desire for an improved product, a prosthesis with a higher permeation resistance potential and greater strength.

U.S. Pat. No. 4,592,755 discloses a prosthesis comprising a leak-proof flexible sac containing a polysiloxane gel and/or oil, said sac comprising a continuous cured polyfluoroalkoxy substituted phosphazene elastomer wall which is substantially impermeable to said gel or oil. In one embodiment described, the prosthesis wall is a two-layer wall, the inner layer comprising a cured polyfluoroalkoxy substituted phosphazene elastomer barrier layer and the outer layer comprising a cured polysiloxane elastomer.

A method of adhering a curable urethane to a room-temperature curable silicone rubber is disclosed in U.S. Pat. No. 4,163,072. The patent describes that, while the silicone rubber is in an uncured state and any solvent present has been allowed to evaporate without curing the silicone rubber, a solvent-resistant cover coating which cures by heat or reaction with moisture, such as polyurethane or epoxy is applied, and then the resulting structure is treated so that the two layers cure simultaneously. The types of silicone rubbers taught as suitable for the technique are limited to room-temperature, moisture-curable silicone rubbers.

U.S. Pat. No. 4,312,920 discloses a blood contacting layer formed by dipping a wax form into a filler-free silicone rubber, curing the silicone rubber, then dipping the coated form into a segmented polyurethane, heat curing the coated form, removing the wax form, then removing the silicone rubber lining, leaving a binary alloy blood contacting surfaced polyurethane sac. The patent states that it appears that the polyurethane solvent has a modifying effect on the filler-free silicone rubber and permits the migration of the polyurethane and silicone rubber species. N-N dimethyl acetamide, formamide, and tetrahydrofuran are mentioned as possible suitable polyurethane solvents.

SUMMARY OF THE INVENTION

Even in view of the currently-available permeation-resistant materials, there remains a need in the medical field for an easy method of making improved permeation-resistant materials which are resistant to the permeation of silicone gels, saline, air, and various other fluids and are suitable for implanting. It is an object of this invention to satisfy this need. It is also an object of this invention to provide a method of making composite materials of silicone elastomer and a barrier-coat elastomer that (1) exhibit minimal swelling or softening in the presence of fluids such as silicone gels or saline; (2) are stronger than the silicone elastomers used currently as barrier coats and are, thus, more resistant to rupture; and (3) can have a continuous outer layer of polydimethyl siloxane elastomer, so that only medically acceptable materials will come in contact with various tissues of the body. The method of this invention is (a) suitable for making strong, permeation-resistant laminates of many shapes, including those that have curves, (b) a way in which to firmly adhere thermoplastic polyurethane, silicone-polyurethane copolymer, or silicone-polycarbonate copolymer elastomer to a cured silicone body even on the surface of hollow silicone elastomer bodies, (c) a way to form clear and transparent laminates from thermoplastic polyurethane, silicone-polyurethane copolymer, or silicone-polycarbonate copolymer elastomer and silicone elastomers, (d) a method which can use materials which are readily available, have a history of use in medical applications, and are relatively economical, and (e) flexible in terms of controlling when curing takes place and the cure rate.

The method of the invention basically entails the steps of: (a) applying a layer of an unvulcanized heat-curable silicone elastomer composition to a cured silicone elastomer substrate, wherein the unvulcanized silicone elastomer composition is covalently-bondable to the cured silicone elastomer substrate, (b) applying a layer of a solvent dispersion of a permeation-resistant elastomer and a first solvent on said layer of unvulcanized silicone elastomer composition to form a three-layered laminate, wherein the permeation-resistant elastomer is selected from the group consisting of polyurethane, silicone-polyurethane copolymer, and silicone-polycarbonate copolymer elastomers, and wherein the first solvent is at least a partial solvent for the unvulcanized silicone elastomer composition, and (c) exposing the three-layered laminate to heat until said unvulcanized silicone elastomer composition is substantially vulcanized.

DETAILED DESCRIPTION OF THE INVENTION

This invention provides a means of adherently coating any size or shape of cured silicone elastomer with a permeation-resistant elastomer selected from the group consisting of polyurethane, silicone-polyurethane copolymer, and silicone-polycarbonate copolymer elastomers. One type of silicone elastomer which is suitable for the cured silicone body for this invention is, e.g., those heat-curable silicone elastomers which cure by reaction between ≡SiH and ≡SiVi ("Vi"=vinyl) groups in the presence of a rare metal catalyst, such as a platinum catalyst. Another suitable type of silicone elastomer is the peroxide-cured silicone elastomer which cures through any of a variety of free-radical reactions. Many types of methyl-containing silicone elastomers may be used for the cured substrate, if a peroxide-curing system is used for the applied unvulcanized silicone elastomer composition discussed below. Rare metal catalyzed, heat-curing silicone elastomers are most preferred due to their physical properties, e.g. tear strength, and to their flexibility in controlling when curing takes place and the cure rate.

The silicone elastomer substrate may be fully or partially cured. If partially-cured, it must be cured enough to allow the silicone body to be fully formed, patched (if needed), manipulated, and to independently maintain its shape when used in the method of this invention. For example, when a mammary prosthesis is being formed by this invention by spreading the silicone and permeation-resistant elastomer on the inside of an envelope by rotating the envelope (called "rotocoating"), the cured silicone body should be cured enough to maintain its shape without permanent distortion when removed from the fabrication equipment and processes and mounted on rotocoating equipment. Best results are obtained when the silicone elastomer is cured just enough to stabilize and maintain its shape, and not completely cured. The remaining uncured reactive sites will allow better bonding to the reactive sites of the subsequently-applied silicone elastomer layer. With systems that use non-selective peroxide catalysts, those that can crosslink polydimethylsiloxanes containing no silicon-vinyl ligands, the degree of cure in the silicone body is of little importance providing the unvulcanized silicone dispersion added contains sufficient quantities of the peroxide to promote vulcanization within the interpenetrating layer and its bonding to the cured silicone body.

For a mammary prosthesis prepared by this invention, a silicone wall thickness of at least 0.005" is preferred. This thickness includes both the initially-cured shell wall thickness and the subsequently-coated layer of heat-curable silicone.

The unvulcanized silicone elastomer applied to the silicone elastomer substrate must be bondable to the silicone elastomer substrate, thus providing for good adhesion of the silicone elastomer layer on the silicone elastomer substrate. Preferably, the unvulcanized silicone elastomer is covalently-bondable to the silicone elastomer substrate. Suitable types of silicone compositions for the unvulcanized silicone elastomer are the aforementioned heat-curable types of silicone elastomers, the rare metal- or peroxide-catalyzed silicone elastomers. To enable the unvulcanized silicone elastomer layer to bond to the silicone substrate, certain combinations of unvulcanized elastomer and vulcanized elastomer are possible. For example, a platinum-curing unvulcanized silicone elastomer composition will bond to a partly-cured platinum-cured silicone elastomer, and a peroxide-curing unvulcanized silicone elastomer composition may bond to either a peroxide-cured silicone elastomer or a rare metal catalyzed elastomer depending upon the composition of the elastomer and the nature of the peroxide. In addition, a rare metal-curing unvulcanized silicone elastomer composition can bond to a peroxide-cured silicone elastomer, so long as the unvulcanized silicone elastomer composition contains some of the effective peroxide also. Similarly, a rare metal-curing unvulcanized silicone elastomer composition can bond to a peroxide-cured silicone elastomer, so long as the peroxide-cured silicone elastomer contains some unreacted vinyl or ≡SiH groups, or both. Another approach to having a platinum-curing unvulcanized silicone elastomer composition bond to a peroxide-cured silicone elastomer is to coat the fully cured silicone elastomer with a non-selective, hot air effective peroxide, such as 2,4 dichlorobenzoyl peroxide. This peroxide would then be available at the interface of the unvulcanized and cured silicones to provide a mechanism of bonding the two silicones by crosslinking.

The unvulcanized silicone compositions may be applied solventless or as a solvent dispersion. Typically, it is preferred to use a high-consistency composition suitable only for application from a solvent dispersion. Solvent dispersions of high molecular weight polymers have lower viscosities for easier application. The types of solvents useful for the silicone elastomer dispersion are those solvents typically suitable for silicones, e.g. aliphatic, aromatic, and chlorinated hydrocarbons and hexamethyldisiloxane. The preferred solvents are the chlorinated solvents, such as 1,1,1 trichloroethane. The solvent for the unvulcanized silicone elastomer does not have to be a solvent for the permeation-resistant elastomer to be applied. The desired concentration of the silicone elastomer dispersion will depend on the specific method used. Preferably, the viscosities and concentrations are such that the dispersion flows freely, allowing it to coat the substrate, but not continue to flow substantially after some evaporation of the solvent. For examples only, and not meant to be limiting, concentrations ranging from about 10–15 weight percent solids, which corresponds to viscosities of about 500–3000 cps. at 25° C. (as measured with a BROOKFIELD viscometer using a #1 spindle at 10 RPM's), have suitable spreading capabilities and drying times.

A multi-molecular layer of the unvulcanized silicone elastomer layer is required for the invention. It has been found that thicknesses of about 0.006 inch of dried unvulcanized silicone elastomer are very suitable for this invention, although the thickness should not be limited to this amount. Typically, more than the minimum required amount of unvulcanized silicone elastomer composition is applied to assure complete coverage of the substrate.

The silicone elastomer dispersion may be applied, e.g., by brushing, spreading, swabbing, dipping, spraying, gravure, rolling, or using any of many known equipment, e.g., kiss roll, air knife, or doctor blade or any other way of causing the silicone elastomer dispersion to become spread on the vulcanized silicone elastomer.

If a solvent dispersion is used as the unvulcanized silicone elastomer layer, the solvent may be left unevaporated or partially or fully evaporated from the uncured silicone elastomer before applying the permeation-resistant elastomer. It is usually desirable before applying the permeation-resistant elastomer/solvent mixture, however, to allow some evaporation so that the layer of uncured silicone elastomer composition is in such a state that it is generally non-flowing. At this state, the permeation-resistant elastomer is more easily applied and there is a better chance that the uncured silicone will remain in contact with the cured silicone. In other words, the uncured silicone elastomer will be less likely to become significantly disturbed by the application of the permeation-resistant elastomer. The amount of solvent removal desired will depend upon each situation, but in general, it is desired to have the uncured silicone elastomer dry enough so that it does not readily flow upon observing after tilting the coated substrate vertically. If the substrate is thin, the uncoated side of the substrate will also no longer feel cool, as it does when solvent is evaporating.

The evaporation of the solvent may be done in various ways. For example, the evaporation may be accelerated by increased temperature, increased air flow, or by lowering pressure, or the evaporation may merely be allowed to happen at room conditions. In the case of making bubble-type body, such as a mammary prosthesis, the coating of the uncured silicone elastomer may be applied to the inside of a cured silicone elastomer bubble, and the solvent will evaporate gradually permeating through the silicone bubble walls, due to its solubility in and permeability through the cured silicone material.

Once the unvulcanized silicone coating has been applied and has developed a suitable viscosity, a coating of permeation-resistant elastomer in solvent dispersion is applied on the silicone coating. The types of permeation-resistant elastomers suitable for use in this invention are those that are non-foaming, solvent-dispersible and elastomeric when set. "Solvent-dispersible" is intended to means that the permeation-resistant elastomer is capable of distributing more or less evenly throughout a medium even if not completely soluble. Solvent-dispersible can mean that from "capable of forming minute particles distinct and separate from one another and suspended in a liquid medium" to that of "being soluble in the liquid medium". Similarly, an elastomer in "solvent dispersion" is intended to mean that the elastomer is distributed more or less evenly throughout a solvent. "When set" is intended to mean when the permeation-resistant elastomer develops its final elastomeric properties either because of evaporation of the solvent or because its final chemical reaction such as polymerization or crosslinking has occurred. It is preferred that the permeation-resistant elastomer be fully-reacted prior to application. "Fully-reacted" is intended to mean that the permeation-resistant elastomer does not require further polymerization or reaction after application to obviate the potential for monomers or other small molecules being present which could leach from the laminate and cause problems biologically. The presence of minor amounts of small molecules in the permeation-resistant elastomer, as is typically found as impurities in materials, may, however, be acceptable depending on the final use of the laminate.

Thermoplastic polyurethane, silicone-polycarbonate copolymer, and silicone-urethane copolymer elastomers, those that soften under heat but are rigid at normal temperature (25° C.) and conditions of stress, are typical of suitable materials. Methods of making thermoplastic polyurethane elastomers can be found in *Polyurethane Elastomers* by C. Hepburn (New York: Applied Science Publishers, 1982), which is hereby incorporated by reference. There are two classes of thermoplastic polyurethanes (or thermoplastic linear urethane block copolymers) usable in this invention. These classes are, namely, Class 1: those that are completely soluble in solvents and possess no chemical crosslinks before or after processing and Class 2: those that possess no crosslinks before processing but if given a heated post-cure will develop a lightly crosslinked structure. After crosslinking the polyurethanes of Class 2, the polyurethanes of Class 2 are insoluble in solvents.

Therefore, Class 2 thermoplastic polyurethanes would not be usable in the invention method to adhere to the layer of unvulcanized silicone elastomer if it is already post-cured.

Thermoplastic silicone polycarbonate copolymer elastomers are known in the art and are described in *Block Copolymers, Overview and Critical Survey* by A. Noshay and J. E. McGrath (New York: Academic Press, 1977), which is hereby incorporated by reference. Thermoplastic silicone polyurethane copolymer elastomers are also known in the art and are described, e.g., in U.S. Pat. Nos. 4,631,329 and 4,793,555 to Gornowicz, et al. and Lee, et al., respectively, which patents are hereby incorporated by reference.

The preferred permeation-resistant elastomers are those that have a modulus of elasticity and potential for elongation as close to the silicone elastomer as possible to improve the adherence of the materials during movement or stretching. Many available polyurethanes have moduli of elasticities greater than the silicone elastomers typically used for fluid-containing prostheses. Therefore, to achieve a better match in elasticity and to maintain the softness of the prostheses, relatively thin layers of polyurethane are usually desired. A specific example of a suitable polyurethane is TECOFLEX® EG-80A Thermoplastic Polyurethane Elastomer available from Thermedics, Inc., Woburn, MA 01888-1799. TECOFLEX® EG-80A polyurethane is a linear, segmented urethane rubbery reaction product of hydrogenated methylene diisocyanate, a 2000 MW polytetramethylene ether glycol, and 1,4 butane diol.

Polyurethanes are usually the preferred material over silicone-polyurethane or silicone-polycarbonate copolymers due to its availability and higher resistance to permeation of gases or liquids (especially silicone fluids). In addition, polyurethanes are stronger and have higher melting and softening points than silicone-polyurethane block copolymers.

Suitable permeation-resistant elastomer solvents or mixture of solvents are those that are generally mutual solvents for both the unvulcanized heat-curable silicone elastomers and the permeation-resistant elastomer used. The solvents will depend on the specific permeation-resistant elastomer employed. As examples, solvents which can be used along with polyurethane are methylene chloride, tetrahydrofuran, dimethylsulfoxide, and toluene. Examples of solvents which can be used in combination with these solvents are dimethylformamide, methyl ethyl ketone, and acetone.

The amount of permeation-resistant elastomer applied will depend on the result desired. Generally, for silicone gel-filled prostheses, with silicone elastomer envelopes, it is desired to have a minimum permeation-resistant elastomer thickness of about 0.001". The thicker the permeation-resistant elastomer, the stronger and the more permeation-resistant the laminate, but the result will also be a higher modulus laminate (less stretchy). Usually for gel-filled prostheses, it is desired to have a soft, flexible feel, so layers of the permeation-resistant elastomer so thick as to cause the prosthesis to feel too stiff would be avoided. The permeation-resistant elastomer dispersion may be applied by the same methods as those described for applying the unvulcanized silicone elastomer coating above. Preferably, however, the permeation-resistant elastomer is applied by a method which involves continual and repetitive movement, such as rotation of random and variable axes (generally known as rotocoating), so that the permeation-resistant elastomer solution is uniformly and randomly applied and interpenetration with the unvulcanized silicone elastomer at the interface is assisted, resulting in better adherence.

The concentration of the permeation-resistant elastomer in solvent used will depend on the specific permeation-resistant elastomer used and other specifics of the method employed. Viscosities similar to those of the unvulcanized silicone elastomer solution are suitable.

Preferably, the solvent is allowed to evaporate from the permeation-resistant elastomer layer before heat curing the laminate. It is preferable that the solvent be evaporated to the extent that the permeation-resistant elastomer coating be substantially non-flowing prior to oven cure to help insure that the coating will remain in the desired place for curing. It is also preferable, before heat-curing the laminate, to dry the permeation-resistant elastomer and silicone dispersion layers substantially to avoid bubbles and blistering caused by any fast evaporation of the solvent during heating of the laminate. The evaporation can be accelerated by heat, lowered pressure, or increased air flow.

After the permeation-resistant elastomer has been applied and is in the desired place for the final product, the laminated body is subject to heat to cure the uncured silicone elastomer and to drive off any remaining solvent present. A practice which avoids bubbling and blistering of quickly evaporating solvent in the elastomers is to place the laminate in a cool oven and then gradually increase the temperature of the oven. This allows slow evaporation of any solvent remaining in the coated elastomers. The temperature to which the body is subjected will depend upon the silicone elastomer composition used, but the temperature must be below the decomposition temperature of the permeation-resistant elastomer or any degradation temperature of the permeation-resistant elastomer or silicone elastomer. If peroxide is included in the permeation-resistant elastomer applied to provide a means for bonding of the permeation-resistant elastomer to the silicone elastomer layer, the cure temperature must be high enough to activate the bonding process.

The result after curing will be a shaped body of silicone having a permeation-resistant elastomer coating firmly-adhered to the silicone body. At this stage, another layer of permeation-resistant elastomer may be adhered to the permeation-resistant elastomer-coated surface either by solvent-welding or heat-welding another layer of permeation-resistant elastomer onto the existing permeation-resistant elastomer coat. To laminate another layer of permeation-resistant elastomer without heat, a solvent mixture of permeation-resistant elastomer is merely coated onto the permeation-resistant elastomer-coated surface, and the solvent is allowed to evaporate and the permeation-resistant elastomer to set. The same permeation-resistant elastomer or a different type of permeation-resistant elastomer than the first layer may be used as the subsequent layer. If solvent-welding is used, the solvent used in the subsequent layer of the permeation-resistant elastomer does not have to be compatible with silicone, but merely has to be compatible with the permeation-resistant elastomers of the first and second layers. Preferably, all of the coatings of permeation-resistant elastomer are heat-annealed to relieve stresses to help avoid wrinkling or partial separation of the coatings.

As mentioned, the method of the invention results in a laminate wherein a permeation-resistant elastomer is firmly adhered to silicone elastomer. It is believed that the two elastomers adhere due to the intermingling or interpenetrating of the permeation-resistant elastomer with the unvulcanized silicone elastomer composition at the interface of the two layers, and once the silicone elastomer layer is vulcanized, the permeation-resistant elastomer is locked into the silicone elastomer. However, generally, the permeation-resistant elastomer layer predominantly provides the properties for good resistance to fluid permeation. The permeation-resistant elastomer and the silicone mix to only a small degree at their interface, so the permeation-resistant elastomer is not diluted throughout with properties of the silicone elastomer.

This invention can be used to make laminates for various applications. For example, the laminates may be used for implantable prostheses, such as mammary or testicular implants, for externally worn mammary prostheses, for gastric balloons, and for tissue expanders.

Now example methods of making mammary prostheses using this invention will be described. Both of these methods result in a prosthesis shell which has silicone elastomer on the outside and polyurethane on the inside surface. These methods take advantage of the fact that silicone elastomers are recognized as suitable implanting material, and therefore, have the silicone on the surface which is to come in contact with the patient's internal tissues. Alternatively, if the prosthesis is to be worn externally, next to the skin, having an appropriate silicone exterior assures minimal irritation.

One such method of making a mammary prosthesis consists of first preparing a silicone elastomer shell by dipping a mammary-shaped mandrel in a silicone elastomer dispersion until a suitable thickness of dispersion is achieved, curing the coated dispersion, then removing the cured shell from the mandrel. Any hole that remains in the shell as a result of the mandrel's handle is patched with silicone elastomer. The patched, cured shell is then injected with a dispersion of heat-curable silicone elastomer and randomly rotated so that the dispersion can evenly coat the inside of the shell (called "rotocoating"). It is often useful to add air into the cured shell to keep it from collapsing and wrinkling during the coating process. The silicone dispersion solvent is then allowed to permeate and evaporate through the shell walls, until the coating is no longer visibly flowable. Next, a solvent solution or dispersion of the polyurethane is injected in the silicone-coated shell. This dispersion, too, is allowed to spread evenly on the inside of the silicone-coated shell by rotating the shell in a bipolar axis mode (rotocoating). Once the polyurethane is evenly coated, the polyurethane solvent is allowed to evaporate through the shell wall for several hours (e.g. 4-6 hours) to assure good evaporation of the solvent. The composite shell is then heat-cured in an oven.

Another suitable method of making a mammary prosthesis would be to first repeatedly dip a mammary-shaped mandrel in a silicone elastomer solvent dispersion, and, after solvent evaporation, minimally cure the elastomer to form a silicone body, optionally remove the cured silicone body from the mandrel, dip the cured silicone body in a heat-curable silicone dispersion, allow the silicone dispersion to dry to a generally non-flowing state, then dip the silicone-coated silicone body in a polyurethane dispersion, and then cure the composite. The cured laminate body is then inverted to place the polyurethane on the inside. The prosthesis shell will require patching at some point during the process, e.g. just before or after curing. The decision whether to use the rotocoating method or the dipping method will depend on the situation. For hollow, collapsible bodies which require patching, such as the shells used for mammary prostheses, it is preferred that the rotocoating method be used since the shell is more apt to maintain its shape and coverage of the patch with the barrier coat is easier to achieve. Additionally, the dipping process has inherent the concern of washing off some of the unvulcanized silicone elastomer layer with the dips into the permeation-resistant elastomer solvent dispersion and does not provide for intermingling of the unvulcanized silicone composition and the polyurethane as well as does the rotocoating method.

The following examples are presented for purposes of illustrating the scope of the invention which is properly delineated in the claims.

EXAMPLE 1

Making a mammary prosthesis using a rotocoating method

A mammary prosthesis using the invention was prepared as follows. A patched, cured silicone elastomer envelope having a volume of 200 $cm^3$ was prepared by first dipping a mandrel in a 13 weight % solvent dispersion of a heat-curable silicone elastomer composition in 1,1,1 trichloroethane, wherein the composition consisted primarily of a dimethylvinylsiloxy endblocked predominantly polydimethylsiloxane containing occasional methylvinylsiloxy units, a copolymer of polydimethyl and polymethylhydrogen siloxane, fumed silica, and a platinum catalyst. The coated elastomer was then cured, the envelope removed from the mandrel, and the resultant hole in the envelope was patched with silicone elastomer of a similar composition. The envelope was then attached to equipment which rotated it, bipolar axis. The envelope was inflated as needed with air to keep it wrinkle-free. Next, 10 $cm^3$ of silicone elastomer dispersion (the same silicone elastomer dispersion as was used to make the envelope) per 100 $cm^3$ of the envelope's volume was inserted into the inflated envelope using a hypodermic needle, and the rotation was activated to coat the inside of the envelope uniformly with the dispersion. Air was added as needed to the envelope to keep the envelope smooth and wrinkle-free. When the 1,1,1 trichloroethane solvent had evaporated such that the silicone coating was no longer flowing and the envelope was not cool to the touch, 10 $cm^3$ of a 6 weight % solution of TECOFLEX® EG-80A Thermoplastic Polyurethane Elastomer in methylene chloride per 100 $cm^3$ of envelope volume was inserted into the envelope. The envelope was again rotated bipolarly to coat the inside surface with the polyurethane solution. When the methylene chloride solvent had evaporated so that the polyurethane was no longer flowing and the envelope was no longer cool to the touch, the coated envelope was placed in a room temperature oven, and the oven was heated gradually to 200° F. The temperature of 200° F. was maintained for two hours to cure the silicone interpenetrating composite. The result was a mammary-shaped silicone elastomer shell having an adhered polyurethane elastomer inner coating.

EXAMPLE 2

Making a testicular prosthesis not according to the invention

A small amount of a 5 weight percent solution of TECOFLEX® EG80A in tetrahydrofuran was injected using a small hypodermic needle into the center of a cured, patched silicone elastomer testicular envelope. The envelope was rotated until the solution uniformly coated its interior. The odor of tetrahydrofuran was clearly detectable through the envelope indicating permeation of the solvent through the silicone and its dissipation. The coating soon dried, but as it dried, it tended to separate from the silicone and eventually shriveled into a tiny ball.

EXAMPLE 3

Making a testicular prosthesis according to the invention

Example 2 was repeated except a small quantity of fresh chlorothene dispersion of heat-vulcanizing silicone elastomer, the same material used to originally fabricate the testicular envelope, was first injected and the envelope rotated to provide a uniform coating. When the chlorothene was essentially dissipated, and without vulcanization of the silicone layer, a small quantity of the polyurethane solution was injected, and the envelope was again rotated to provide a uniform coating. After allowing the envelope to stand overnight, it was placed in an oven at 250° F. After removal from the oven, separation between the polyurethane and the silicone generally did not occur, and the laminated film was clear, transparent, highly glossy on the interior, and firmly adherent.

EXAMPLE 4

Measurements of Bleed Resistance

A 200 cm³-volume envelope was prepared by the procedure described in Example 1, and the envelope was then injected with a liquid silicone gel composition using a syringe. The silicone gel contained predominantly free polydimethylsiloxane fluid having a viscosity of about 1000 cst. at 25° C., and a small portion of silicone elastomer composition. A small amount of silicone adhesive was applied to the needle punch hole. The gel-filled envelope was then placed in an oven for four hours at 225° F. to cure the gel. Similarly, a 260 cm³-volume gel-filled implant having only a silicone elastomer wall (i.e. no laminations) was also prepared using the same silicone elastomer for the envelope as that described for the envelope in Example 1.

The outer surface of both the silicone elastomer implant and the silicone elastomer/polyurethane implant were washed thoroughly with isopropyl alcohol. The implants were then placed in a hot air oven set at 100° C. for 2 hours to remove any residual alcohol. The implants were then weighed to the nearest 1/100 gram. The implants were then each placed in a wide-mouth screw-top one-gallon glass jar along with 500 grams CELITE SUPERFLOSS® diatomaceous earth, placed on a jar roll mill and rolled for 24 hours. The implants were than removed and their surfaces thoroughly cleaned with a cloth saturated with a 5 weight % solution of IVORY® dishwashing liquid in distilled water to remove any adherent diatomaceous earth. The implants were then conditioned for 2 hours in a 100° C. oven and then weighed. The rolling, cleaning, heat conditioning, and weighing were repeated several times to measure weight losses over time. No additional diatomaceous earth was added after the initial 500 grams. Table 1 presents the cumulative weight loss vs. time for both the solely-silicone implant and the polyurethane-coated silicone implant. To obviate any difference due to size of the implant, calculations were made to determine the % weight loss relative to the original weight of the implants, where % weight loss=(cumulative weight loss×100)/(original weight). Table 2 gives the % weight losses corresponding to the values in Table 1. The data clearly demonstrates the effectiveness of the invention in preparing a permeation-resistant gel-filled implant.

TABLE 1

| | Silicone-Walled Implant | | Polyurethane-Coated Silicone Walled Implant | |
|---|---|---|---|---|
| Time (hrs) | Weight (gms) | Cumulative Wt. Loss (gms) | Weight (gms) | Cumulative Wt. Loss (gms) |
| 0 | 250.24 | 0.0 | 194.28 | 0.0 |
| 24 | 248.89 | 1.35 | 193.86 | 0.42 |
| 48 | 247.54 | 2.70 | — | — |
| 120 | 245.61 | 4.63 | 193.32 | 0.96 |
| 144 | 244.23 | 6.01 | — | — |
| 192 | — | — | 192.98 | 1.3 |

TABLE 2

| | Silicone-Walled Implant | Polyurethane-Coated Silicone Walled Implant |
|---|---|---|
| Time (hrs) | Weight Loss (%) | Weight Loss (%) |
| 0 | 0 | 0 |
| 24 | 0.53 | 0.22 |
| 48 | 1.06 | — |
| 120 | 1.82 | 0.49 |
| 144 | 2.36 | — |
| 192 | — | 0.67 |

These and other variations of the present invention may be made which fall within the scope of the appended claims even though such variations were not specifically discussed above.

That which is claimed is:

1. A method of making a permeation-resistant silicone elastomer-containing laminate for medical devices comprising the steps of:
   (a) applying a layer of an unvulcanized heat-curable silicone elastomer composition to a cured silicone elastomer substrate, wherein said unvulcanized silicone elastomer composition is bondable to said cured silicone elastomer substrate,
   (b) applying a layer of a solvent dispersion of a permeation-resistant elastomer and a first solvent on said layer of unvulcanized silicone elastomer composition to form a three-layered elastomeric laminate, wherein said permeation-resistant elastomer is selected from the group consisting of polyurethane, silicone-polyurethane copolymer, and silicone-polycarbonate copolymer, and wherein said first solvent is at least a partial solvent for said unvulcanized silicone elastomer composition, and
   (c) exposing said three-layered elastomeric laminate to heat until said unvulcanized silicone elastomer composition is substantially vulcanized.

2. A method as claimed in claim 1 wherein said unvulcanized silicone elastomer composition is dispersed in a second solvent.

3. A method as claimed in claim 2 further comprising the step, after the applying step (a) and before the applying step (b), of evaporating said second solvent until said unvulcanized silicone elastomer composition layer is substantially non-flowing.

4. A method as claimed in claim 1 further comprising, after said applying step (b) and before said exposing step (c), the step of evaporating said first solvent until said permeation-resistant elastomer layer is substantially non-flowing.

5. A method as claimed in claim 4 further comprising, after said applying step (b) and before said permeation-resistant elastomer layer is substantially non-flowing, the step of moving said substrate to assist the mixing of said permeation-resistant elastomer dispersion with said unvulcanized silicone elastomer composition at their interface.

6. A laminate prepared by the method of claim 5.

7. A method of making a hollow permeation-resistant silicone elastomer-containing body for medical devices comprising the steps of:
(a) applying a layer of an unvulcanized heat-curable silicone elastomer composition on the inside of a hollow, cured silicone elastomer substrate, wherein said unvulcanized silicone elastomer composition is bondable to said cured silicone elastomer substrate,
(b) applying a layer of a solvent dispersion of a permeation-resistant elastomer and a first solvent on said layer of unvulcanized silicone elastomer composition to form a three-layered elastomeric body, wherein said permeation-resistant elastomer is selected from the group consisting of polyurethane, silicone-polyurethane copolymer, and silicone-polycarbonate copolymer, and wherein said first solvent is at least a partial solvent for said unvulcanized silicone elastomer composition, and
(c) exposing said three-layered elastomeric body to heat until said unvulcanized silicone elastomer composition is substantially vulcanized.

8. A laminate prepared by the method of claim 7.

9. A method of making a fluid-containing body comprising the steps of:
(a) applying a layer of an unvulcanized heat-curable silicone elastomer composition to the inside surface of a hollow substrate of cured silicone elastomer, wherein said unvulcanized silicone elastomer composition is bondable to said cured silicone elastomer substrate,
(b) applying a layer of a solvent dispersion of a permeation-resistant elastomer and a first solvent on said layer of unvulcanized silicone elastomer composition to form a three-layered laminated substrate, wherein said permeation-resistant elastomer is selected from the group consisting of polyurethane, silicone-polyurethane copolymer, and silicone-polycarbonate copolymer, and wherein said first solvent is at least a partial solvent for said unvulcanized silicone elastomer composition, and
(c) exposing said three-layered laminated substrate to heat until said unvulcanized silicone elastomer composition is substantially vulcanized, and
(d) filling said cured three-layered laminated substrate with fluid.

10. A method as claimed in claim 9 wherein said fluid is a silicone gel.

11. A fluid-containing body prepared by the method of claim 10.

12. A fluid-containing body prepared by the method of claim 9.

13. A method as claimed in claim 9 wherein said unvulcanized silicone elastomer composition is dispersed in a second solvent.

14. A method as claimed in claim 13 further comprising the step, after the applying step (a) and before the applying step (b), of evaporating said second solvent until said unvulcanized silicone elastomer composition layer is substantially non-flowing.

15. A method as claimed in claim 9 further comprising, after said applying step (b) and before said exposing step (c), the step of evaporating said first solvent until said permeation-resistant elastomer layer is substantially non-flowing.

16. A method as claimed in claim 15 further comprising, after said applying step (b) and before said permeation-resistant elastomer layer is substantially non-flowing, the step of moving said hollow substrate to assist the mixing of said permeation-resistant elastomer dispersion with said unvulcanized silicone elastomer composition at their interface.

17. A method as claimed in claim 9 wherein said permeation-resistant elastomer is fully-reacted when applied in step (b).

18. A method as claimed in claim 9 wherein said permeation-resistant elastomer is a thermoplastic linear urethane block copolymer.

19. A method as claimed in claim 9 wherein said fluid is a silicone gel.

20. A fluid-containing body prepared by the method of claim 19.

21. A method as claimed in claim 1 wherein said permeation-resistant elastomer is fully-reacted when applied in step (b).

22. A method as claimed in claim 1 wherein said permeation-resistant elastomer is a thermoplastic linear urethane block copolymer.

23. A method as claimed in claim 1 wherein said permeation-resistant elastomer is polyurethane.

24. A laminate prepared by the method of claim 23.

25. A method as claimed in claim 1 wherein said permeation-resistant elastomer is a silicone-polyurethane copolymer.

26. A laminate prepared by the method of claim 25.

27. A method as claimed in claim 1 wherein said permeation-resistant elastomer is a silicone-polycarbonate copolymer.

28. A laminate prepared by the method of claim 27.

29. A laminate prepared by the method of claim 1.

30. A method of making a fluid-containing body comprising the steps of:
(a) applying a layer of an unvulcanized silicone elastomer composition to the inside surface of a hollow substrate of cured silicone elastomer, wherein said unvulcanized silicone elastomer composition is bondable to said cured silicone elastomer substrate,
(b) applying a layer of a solvent dispersion of a permeation-resistant elastomer and a first solvent on said layer of unvulcanized silicone elastomer composition to form a three-layered laminated body, wherein said permeation-resistant elastomer is selected from the group consisting of polyurethane, silicone-polyurethane copolymer, and silicone-polycarbonate copolymer, and wherein said first solvent is at least a partial solvent for said unvulcanized silicone elastomer composition, and (c) curing said three-layered body until said unvulcanized silicone elastomer composition is substantially vulcanized, and (d) filling said cured three-layered laminated body with fluid.

31. A fluid-containing body prepared by the method of claim 30.

32. A method as claimed in claim 30 wherein said unvulcanized silicone elastomer composition is dispersed in a second solvent.

33. A method as claimed in claim 32 further comprising the step, after the applying step (a) and before the applying step (b), of evaporating said second solvent until said unvulcanized silicone elastomer composition layer is substantially non-flowing.

34. A method as claimed in claim 30 further comprising, after said applying step (b) and before said curing step (c), the step of evaporating said first solvent until said permeation-resistant elastomer layer is substantially non-flowing.

35. A method as claimed in claim 34 further comprising, after said applying step (b) and before said permeation-resistant elastomer layer is substantially non-flowing, the step of moving said hollow substrate to assist the mixing of said permeation-resistant elastomer dispersion with said unvulcanized silicone elastomer composition at their interface.

36. A method as claimed in claim 30 wherein said permeation-resistant elastomer is fully-reacted when applied in step (b).

37. A method as claimed in claim 30 wherein said permeation-resistant elastomer is a thermoplastic linear urethane block copolymer.

* * * * *